US010610514B2

(12) United States Patent
Kim et al.

(10) Patent No.: US 10,610,514 B2
(45) Date of Patent: Apr. 7, 2020

(54) COMPOSITION COMPRISING COMPOUND INHIBITING INTERACTIONS OF MBD2 AND P66α FOR ANTI-METASTASIS AND PREVENTION AND TREATMENT OF CANCER DISEASE

(71) Applicant: Industry-University Cooperation Foundation Hanyang University, Seoul (KR)

(72) Inventors: Chul Geun Kim, Seoul (KR); Min Young Kim, Incheon (KR); Young Su Lim, Jeollabuk-do (KR); Dae Hyun Ha, Seoul (KR); Young Yiul Lee, Seoul (KR); Buom Yong Ryu, Gyeonggi-do (KR); Vladimir Uversky, Tampa, FL (US); Insung Na, Gyeonggi-do (KR); Yu Chen, Tampa, FL (US); Arjan van der Vaart, Tampa, FL (US)

(73) Assignees: Industry-University Cooperation Foundation Hanyang University (KR); University of South Florida, Tampa, FL (US)

(*) Notice: Subject to any disclaimer, the term of this patent is extended or adjusted under 35 U.S.C. 154(b) by 0 days.

(21) Appl. No.: 15/821,984

(22) Filed: Nov. 24, 2017

(65) Prior Publication Data
US 2018/0250266 A1 Sep. 6, 2018

(30) Foreign Application Priority Data

Nov. 24, 2016 (KR) .................. 10-2016-0157163
Nov. 24, 2016 (KR) .................. 10-2016-0157164

(51) Int. Cl.
*A61K 31/40* (2006.01)
*A61P 35/02* (2006.01)
*A61K 31/357* (2006.01)

(52) U.S. Cl.
CPC ............ *A61K 31/40* (2013.01); *A61K 31/357* (2013.01); *A61P 35/02* (2018.01)

(58) Field of Classification Search
CPC ........ A61K 31/40; A61K 31/357; A61P 35/02
See application file for complete search history.

(56) References Cited

FOREIGN PATENT DOCUMENTS

WO   WO2014/194280   * 12/2014   ........... A61K 31/325

OTHER PUBLICATIONS

Dovey et al (PNAS | May 4, 2010 | vol. 107 | No. 18) (Year: 2010).*
Fu et al., "The Twist/Mi2/NuRD protein complex and its essential role in cancer metastasis", Cell Research (2011) 21:275-289.
(Continued)

*Primary Examiner* — Angela C Brown-Pettigrew
(74) *Attorney, Agent, or Firm* — Adsero IP

(57) ABSTRACT

The present invention relates to a composition including an inhibitor against the function of an Mi-2/NuRD chromatin remodeling complex for inhibiting metastasis and preventing and treating cancer diseases, and more particularly, the composition may inhibit the MBD2-p66α (GATAD2A) interaction by means of the Mi-2/NuRD CRC function inhibitor, and thus is expected to be effectively used as a composition capable of inhibiting metastasis and preventing and treating cancer diseases.

6 Claims, 17 Drawing Sheets

(56) References Cited

OTHER PUBLICATIONS

Hendrich et al., "Closely related proteins MBD2 and MBD3 play distinctive but interacting roles in mouse development", downloaded from Genesdev.cshlp.org on Nov. 22, 2017—Published by Cold Spring Harbor Laboratory Press, pp. 710-723.
Kang et al., "PIAS1 regulates CP2c localization and active promoter complex formation in erythroid cell-specific α-globin expression", Nucleic Acids Research, 2010, vol. 38, No. 16, pp. 5456-5471.
Kang et al., "Identification and characterization of four novel peptide motifs that recognize distinct regions of the transcription factor CP2", FEBS Journal 272 (2005) 1265-1277.
Kang et al., "Erythroid Cell-Specific α-Globin Gene Regulation by the CP2 Transcription Factor Family", Molecular and Cellular Biology, Jul. 2005, vol. 25, No. 14, p. 6005-6020.
Mian et al. "Methyl-Binding Domain Protein 2-Dependent Proliferation and Survival of Breast Cancer Cells", Mol Cancer Res; 9(8) Aug. 2011, pp. 1152-1162.
Sansom et al., "Deficiency of Mbd2 suppresses intestinal tumorigenesis", Nature Genetics vol. 34, No. 2, Jun. 2003, pp. 145-147.
Slack et al., "Antisense MBD2 gene therapy inhibits tumorigenesis", J. Gene Med. 2002; 4: 381-389.

* cited by examiner

[FIG. 1A]
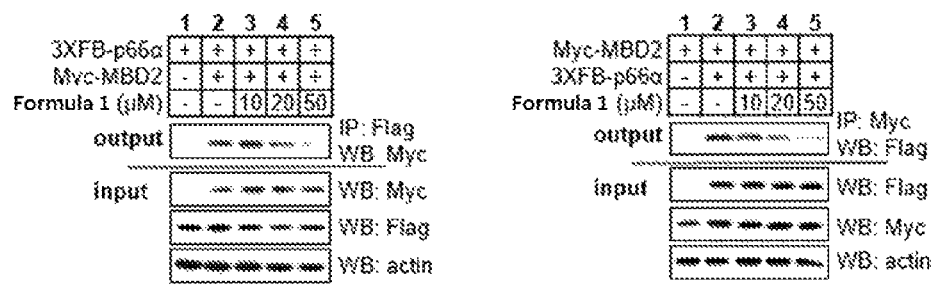
[FIG. 1B]
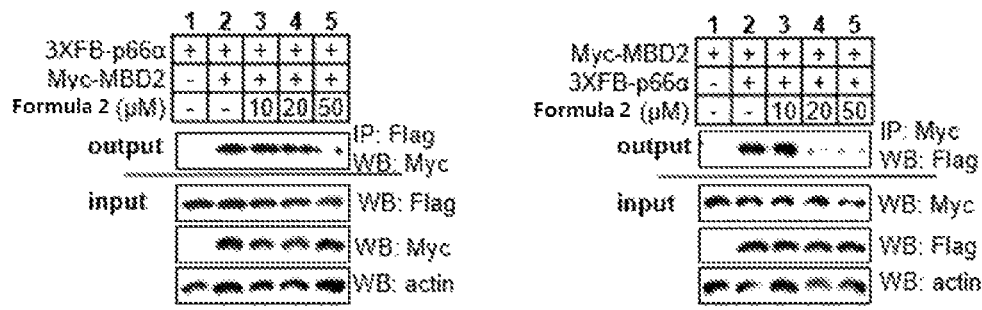

[FIG. 2A]
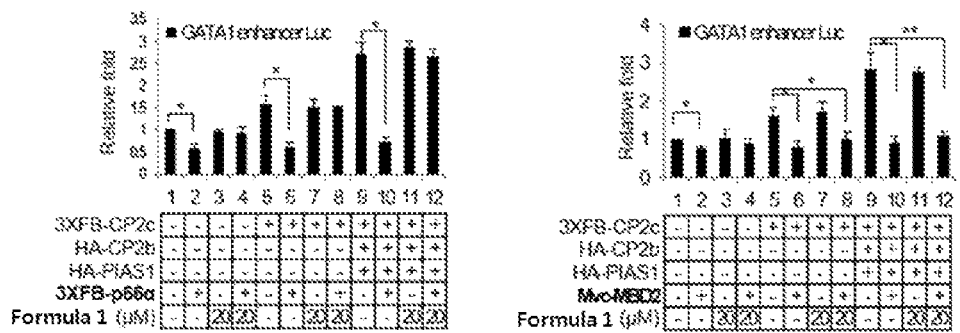
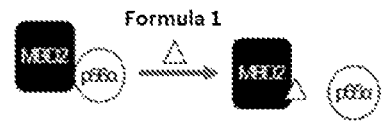
[FIG. 2B]
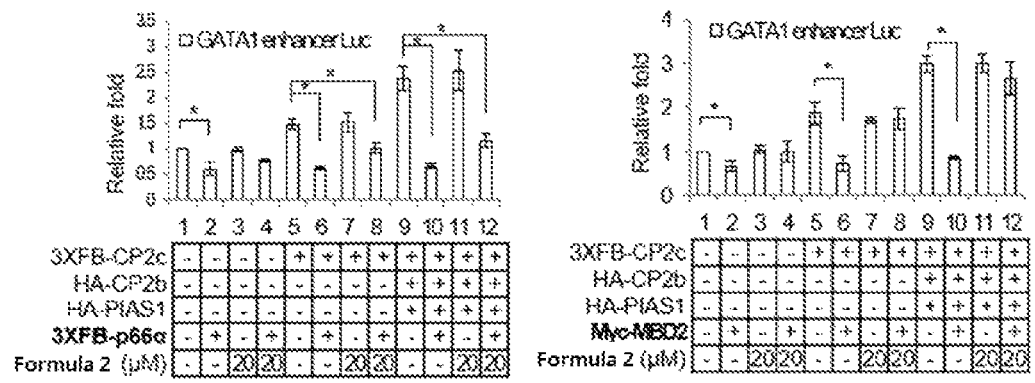
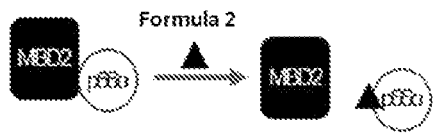

[FIG. 3A]
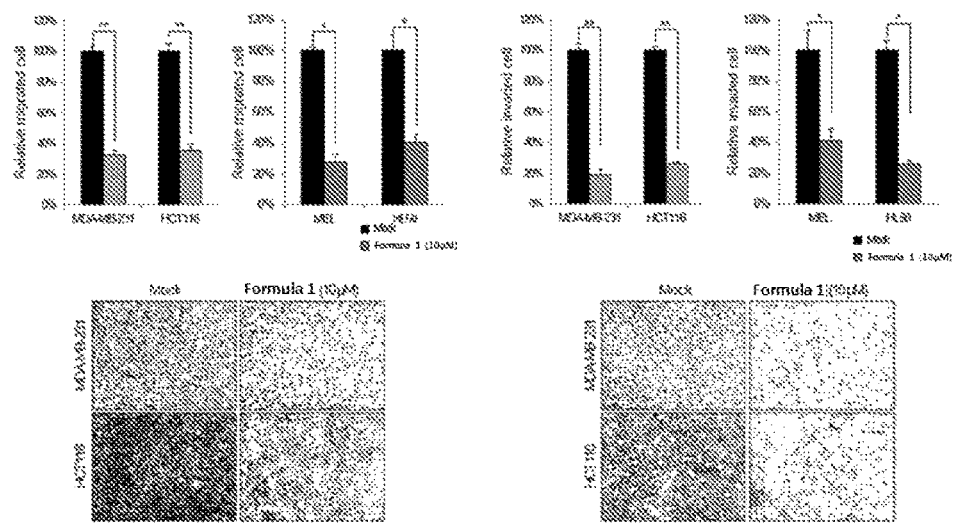
[FIG. 3B]
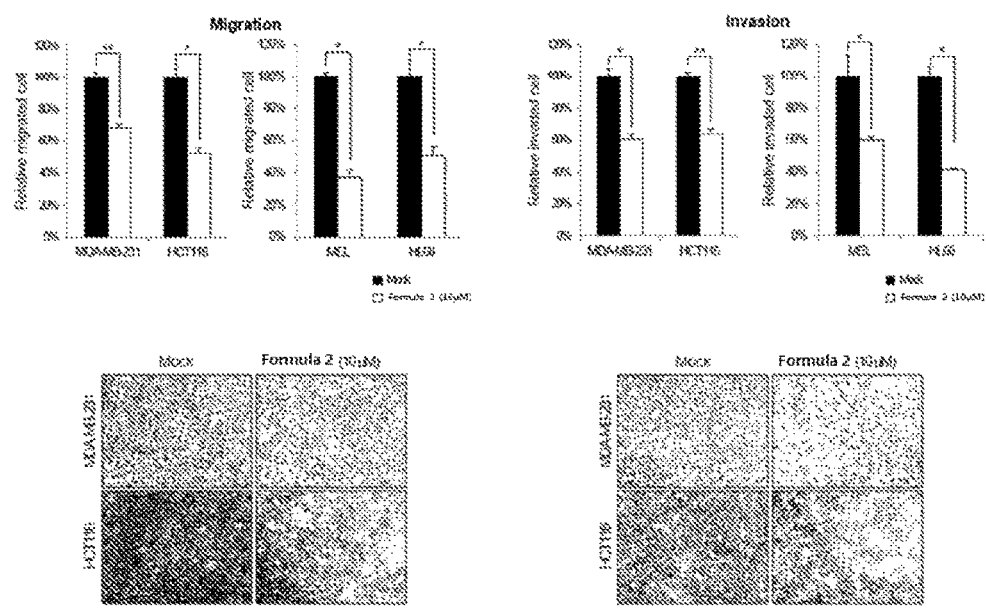

【FIG. 4A】
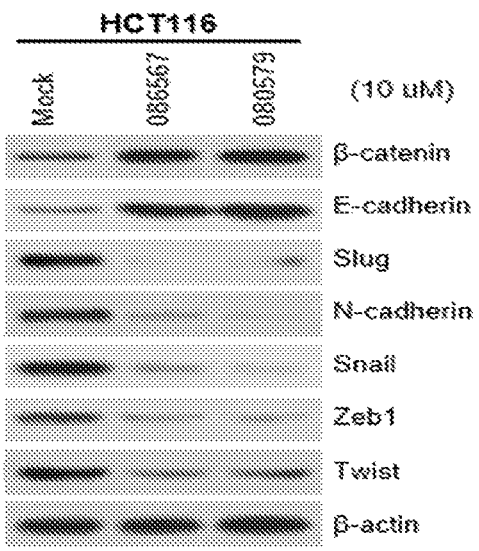
【FIG. 4B】
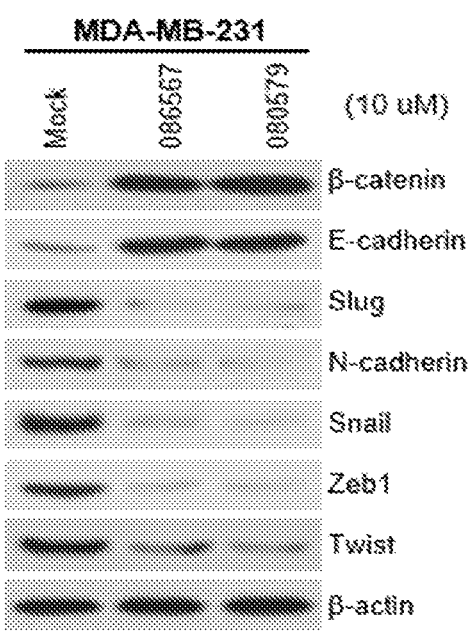

[FIG. 5A]
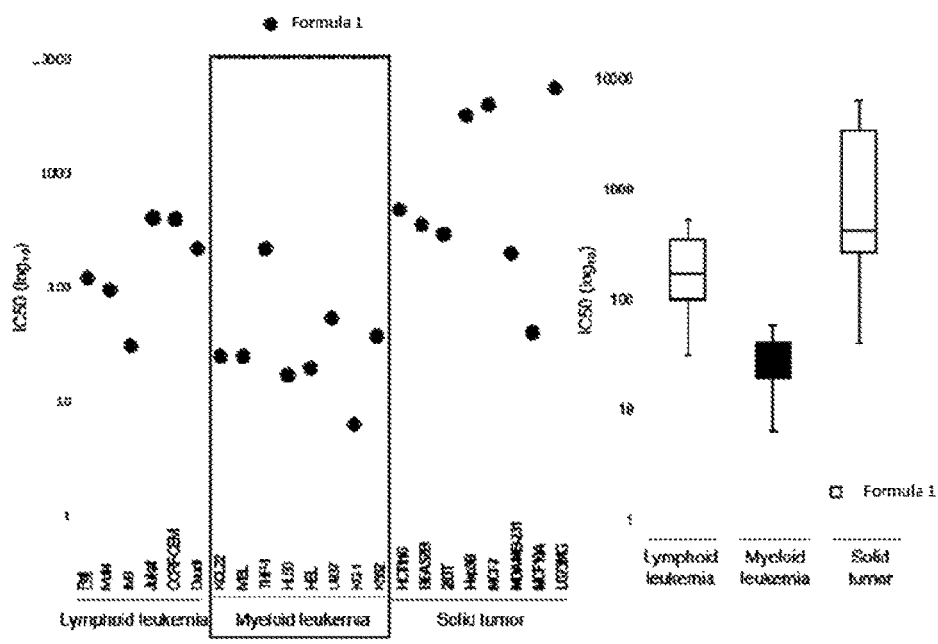
[FIG 5B]
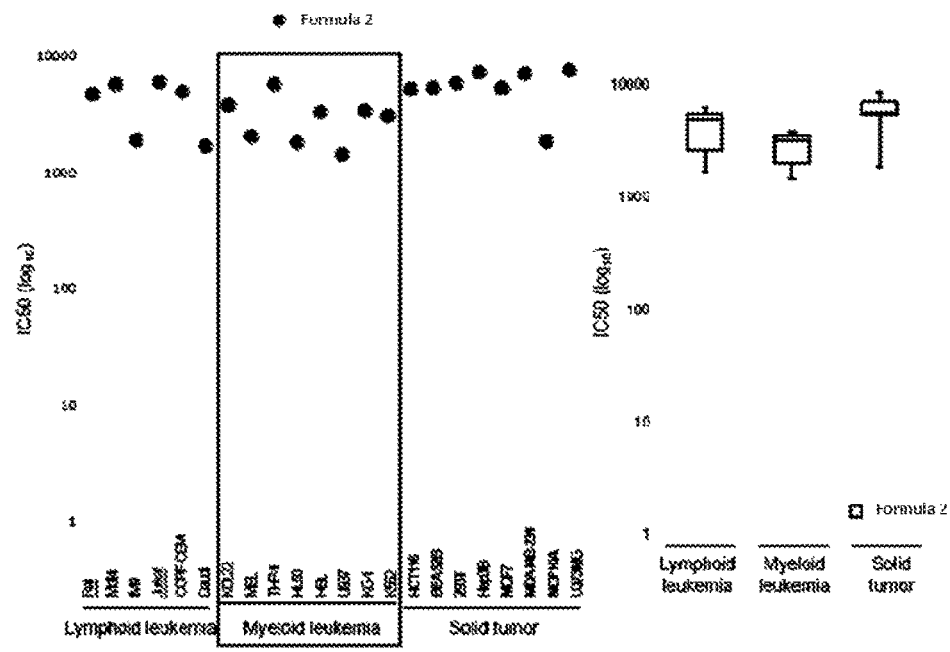

[FIG. 6A]
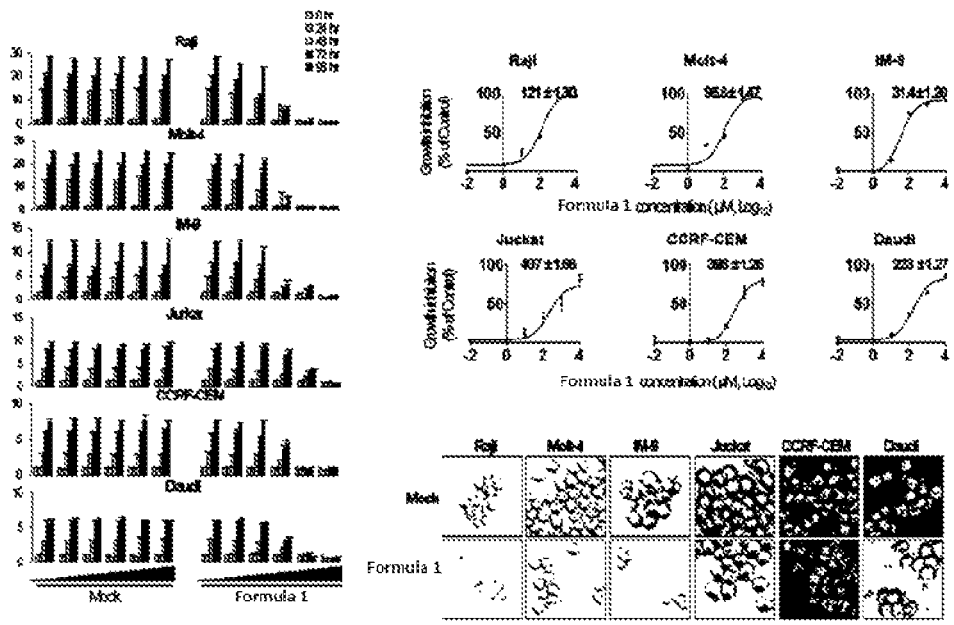
[FIG. 6B]
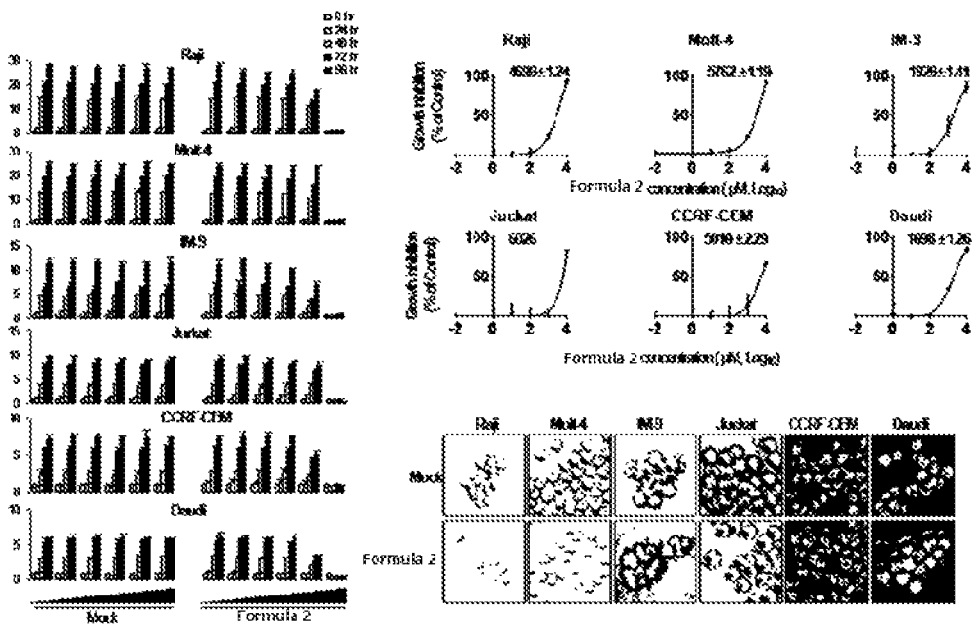

[FIG. 7A]
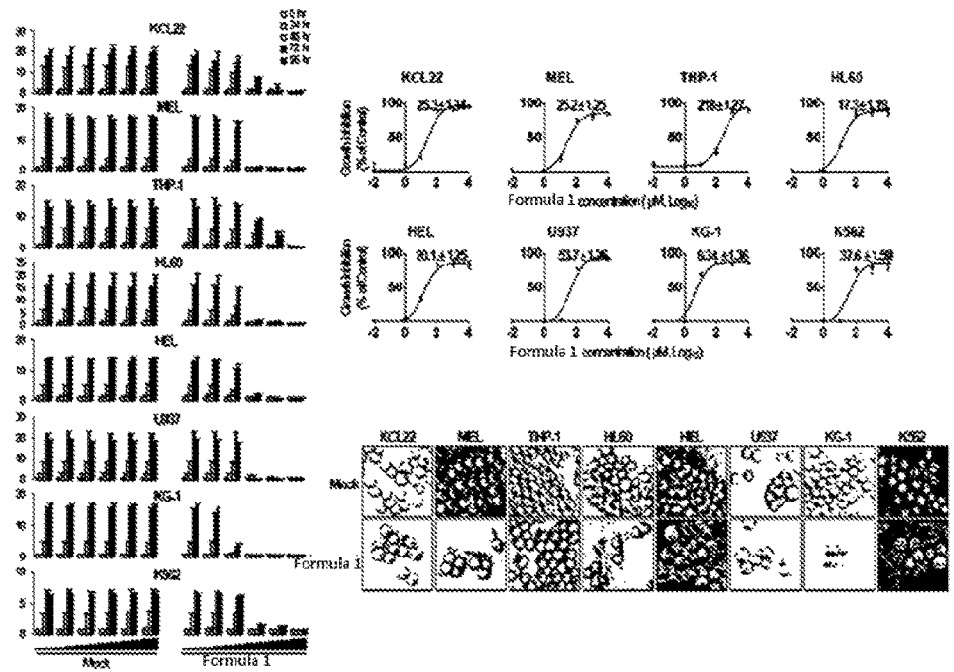
[FIG. 7B]
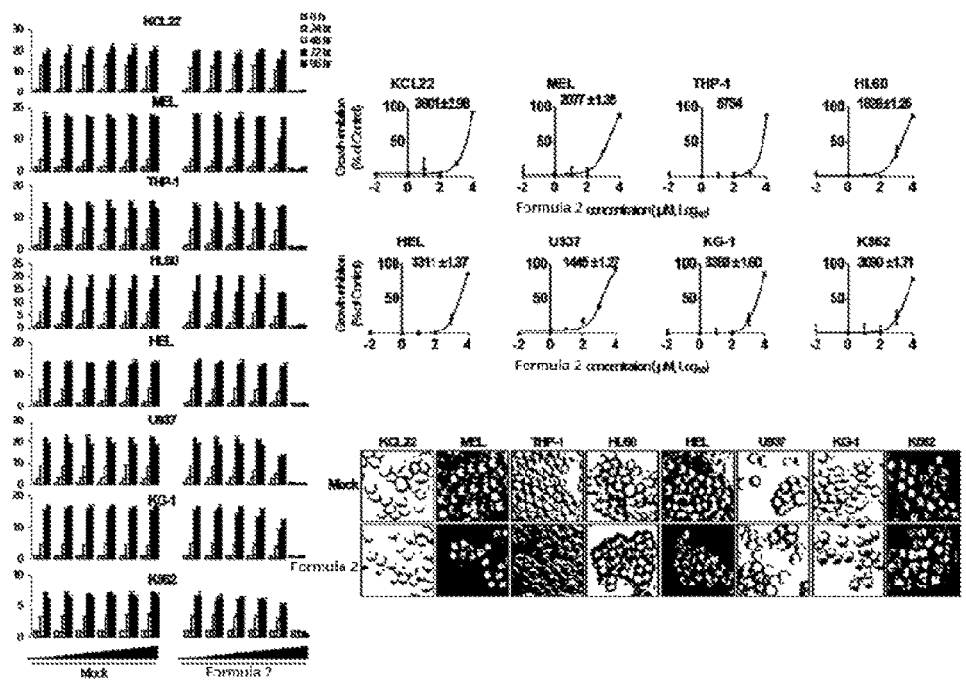

[FIG. 8A]
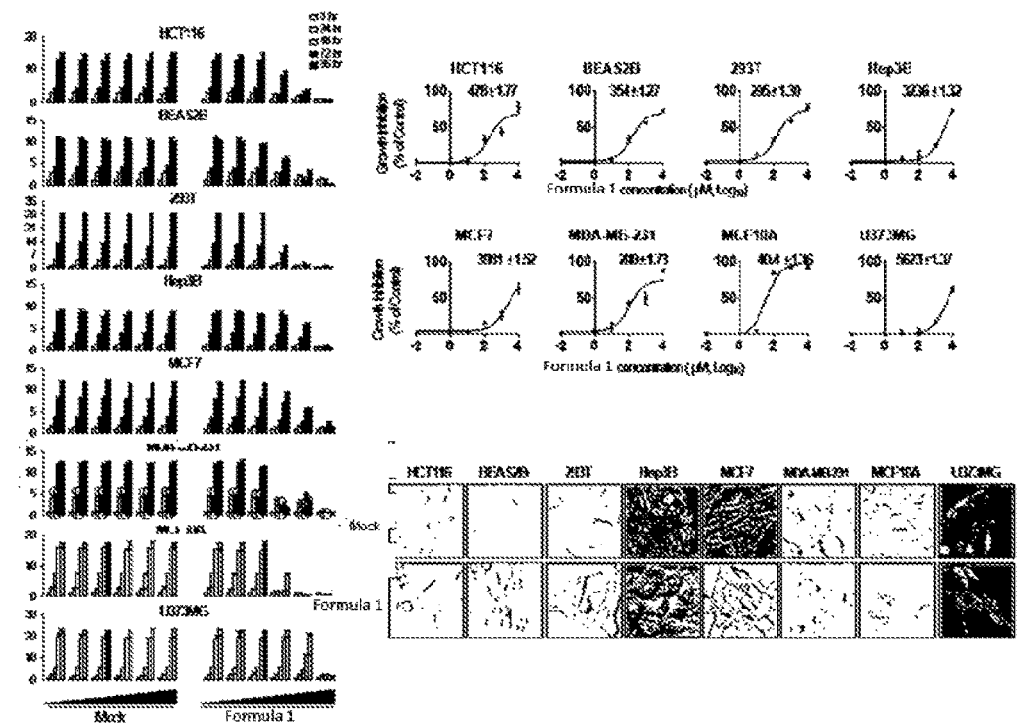
[FIG. 8B]
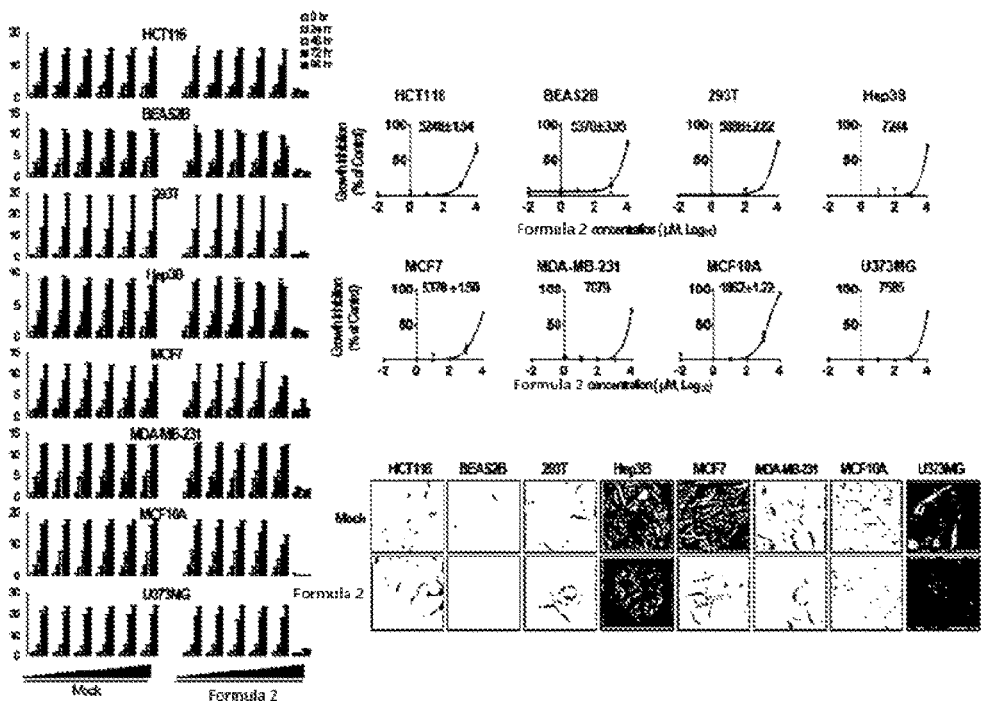

[FIG. 9A]
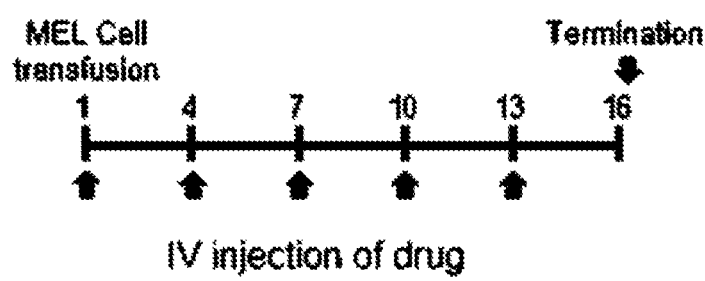
[FIG. 9B]
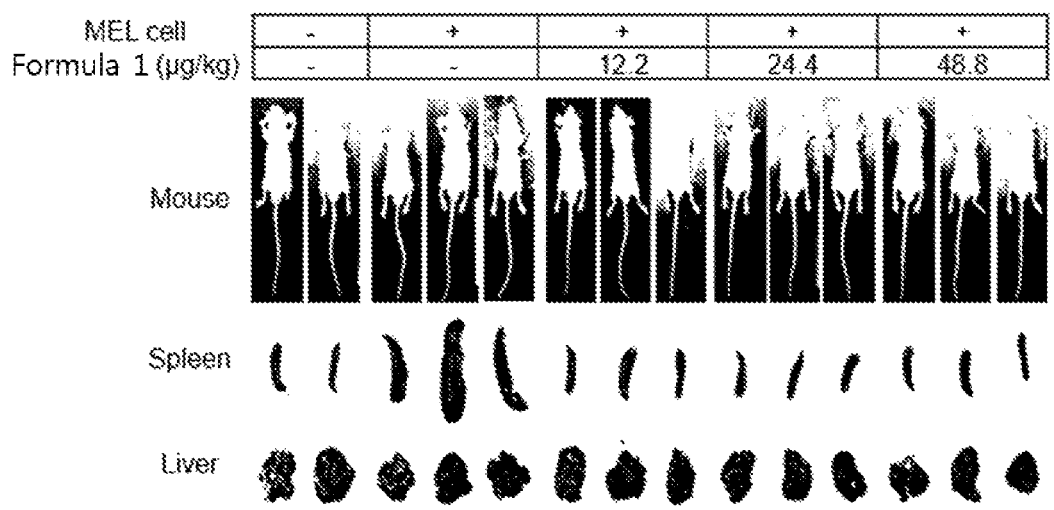

[FIG. 9C]
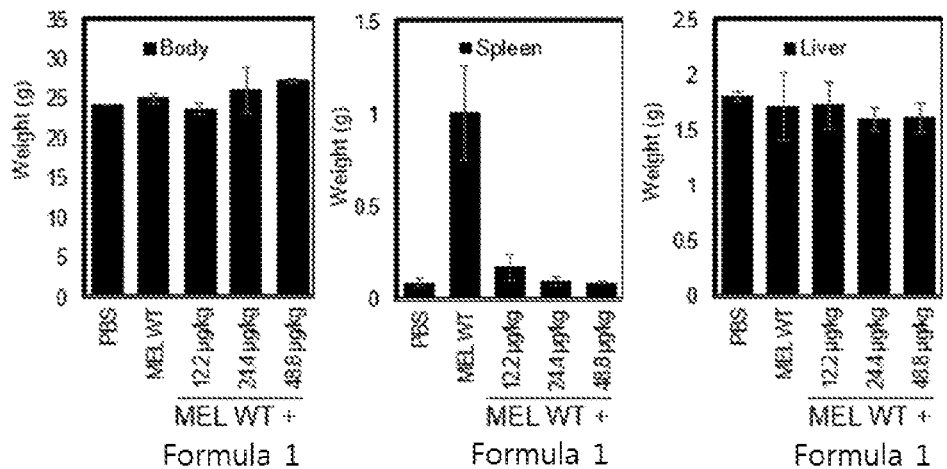
[FIG. 9D]
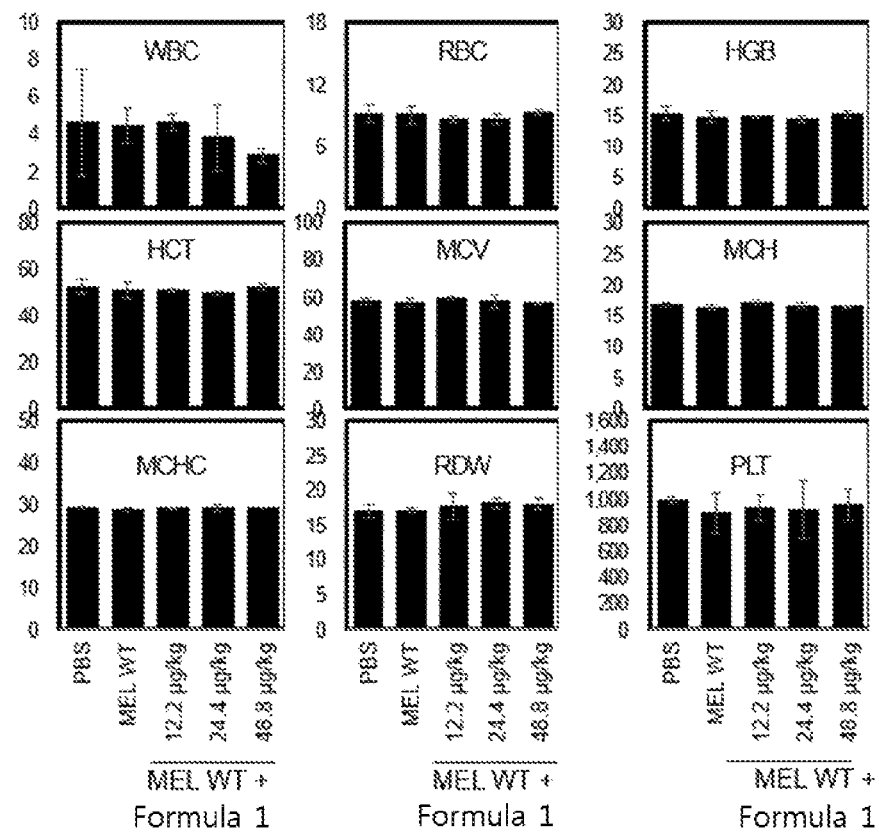

[FIG. 9E]
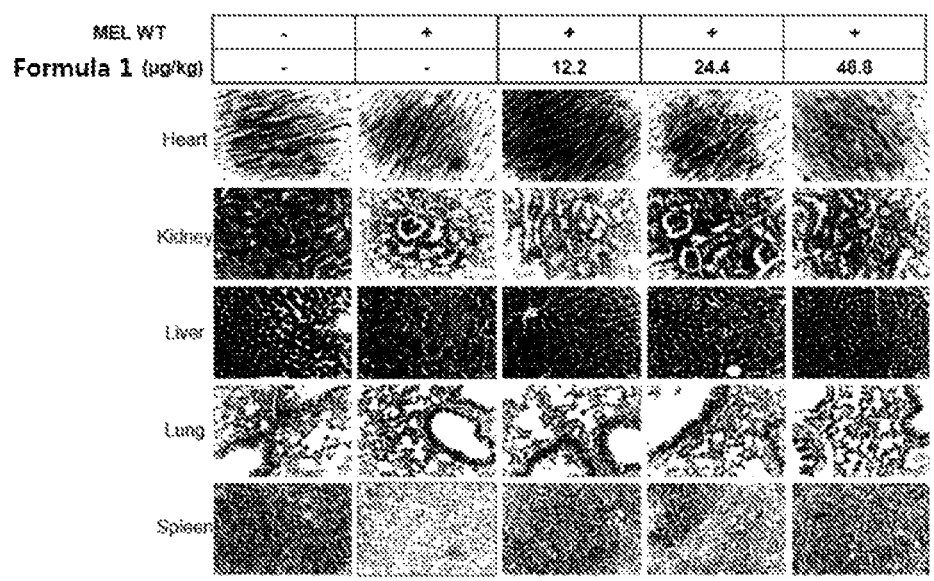
[FIG. 9F]
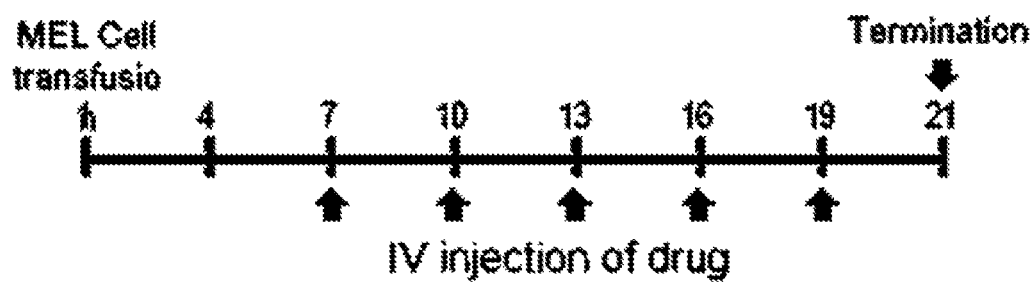

[FIG. 9G]
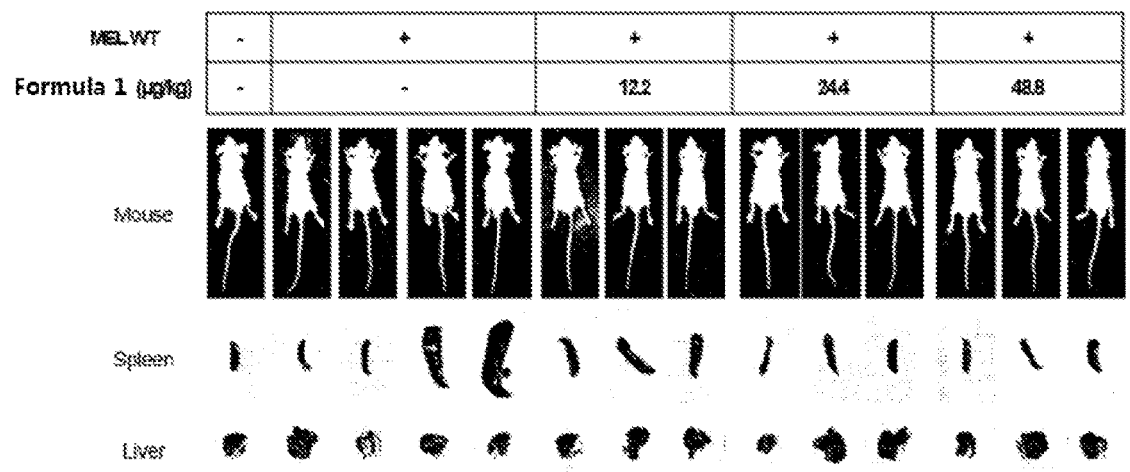
[FIG. 9H]
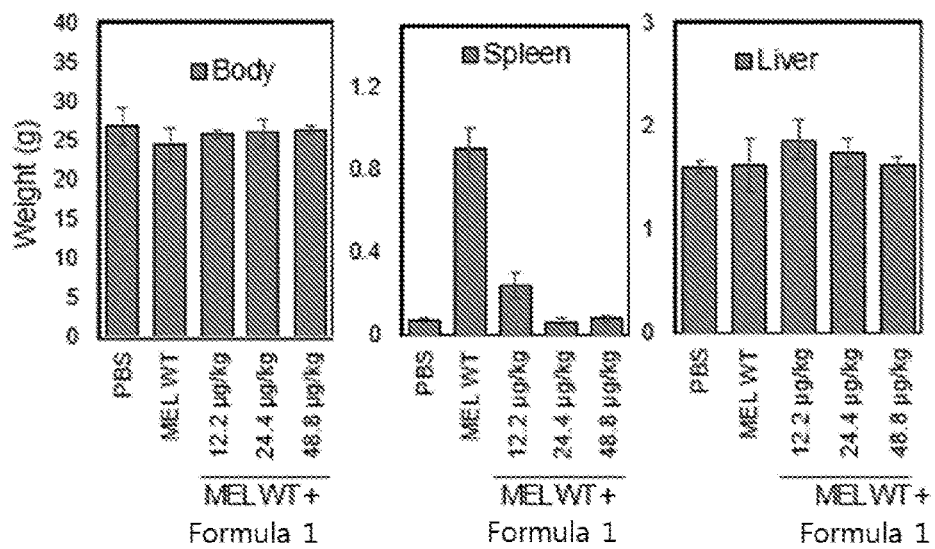

[FIG. 9I]
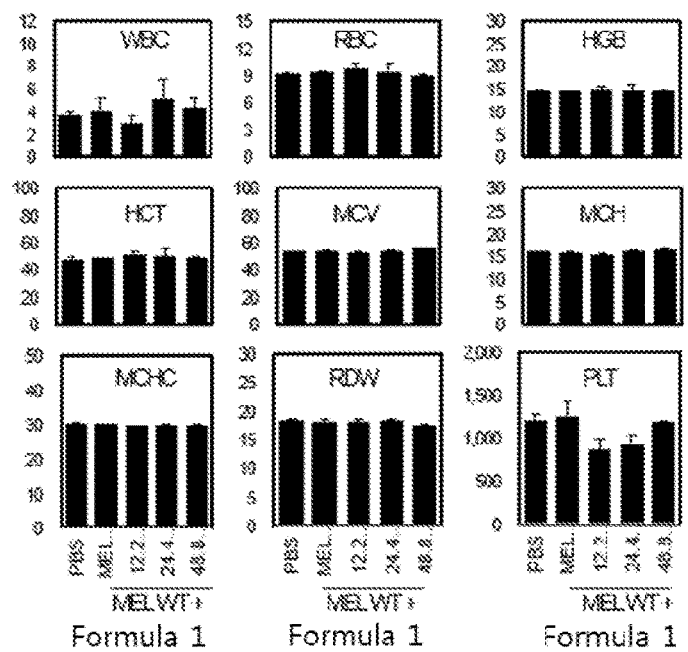
[FIG. 9J]
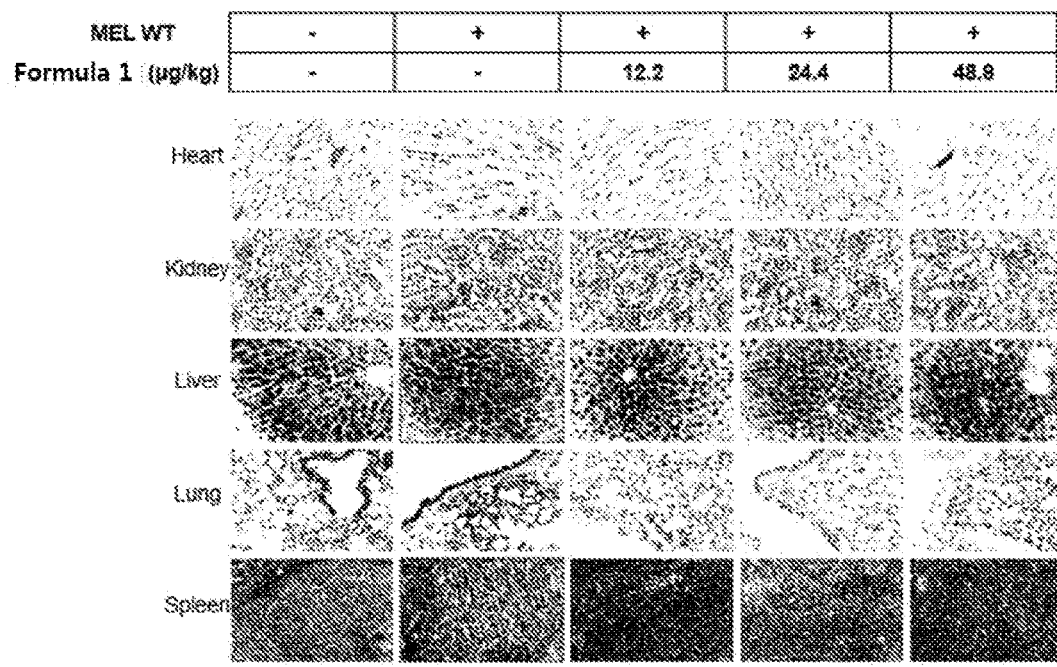

[FIG. 10A]
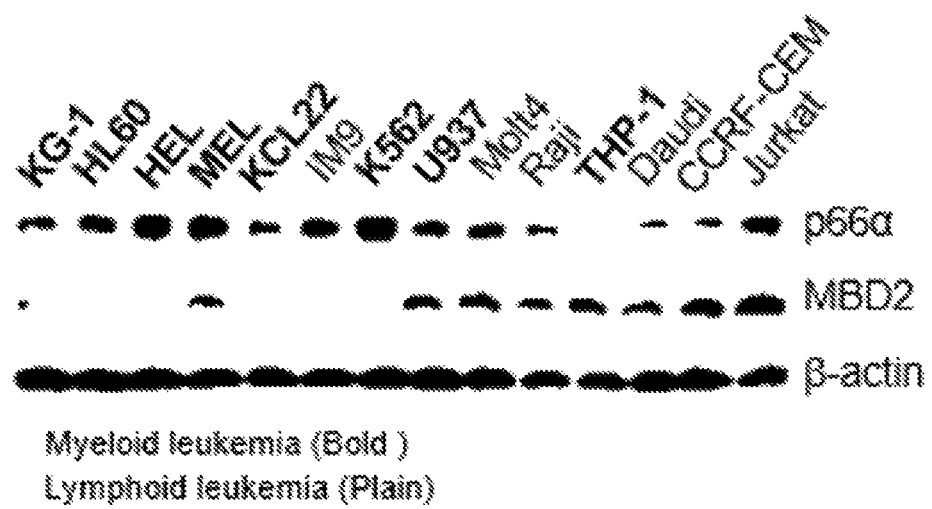
Myeloid leukemia (Bold)
Lymphoid leukemia (Plain)
[FIG. 10B]
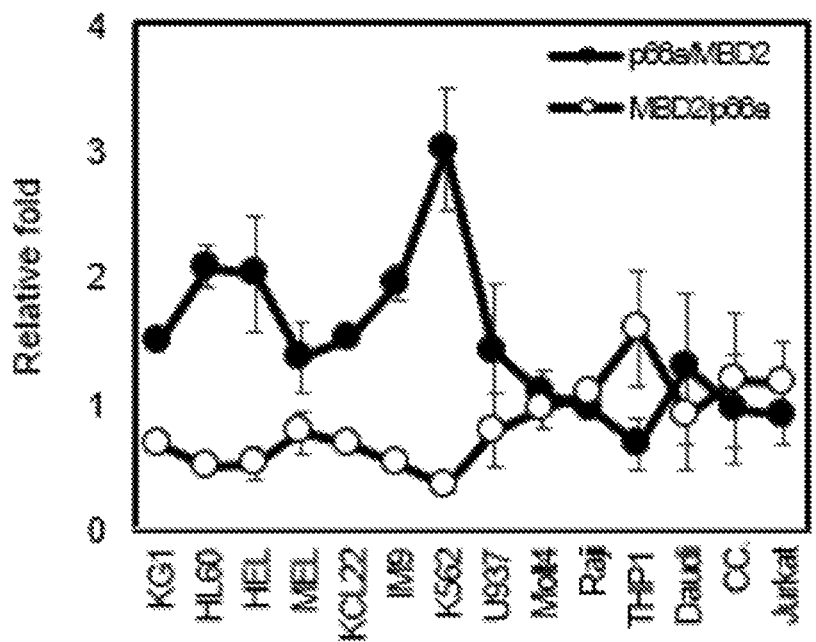

[FIG. 11]
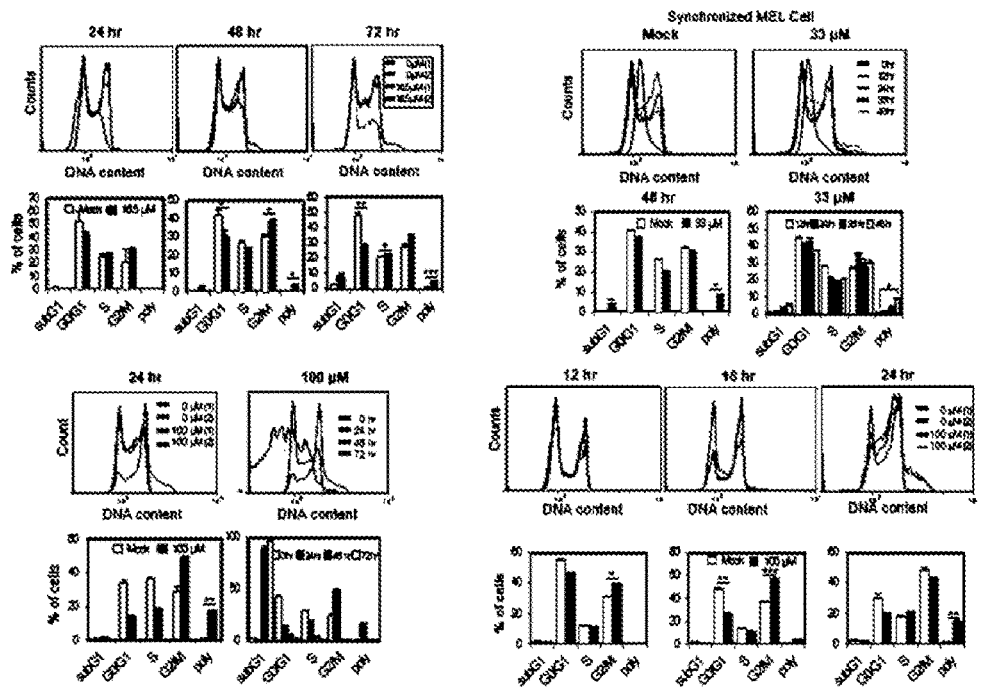
[FIG. 12]
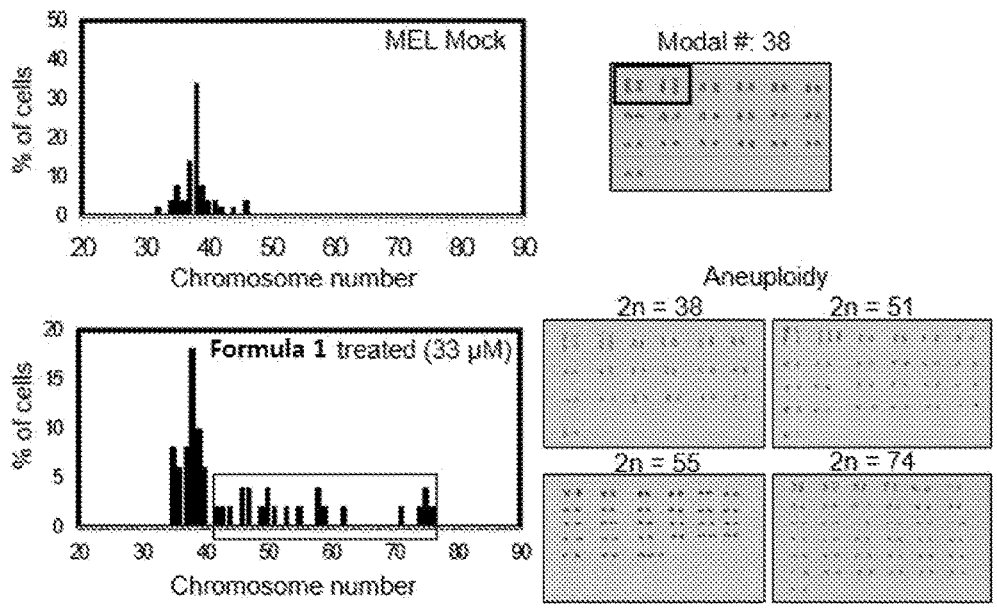

[FIG.13]
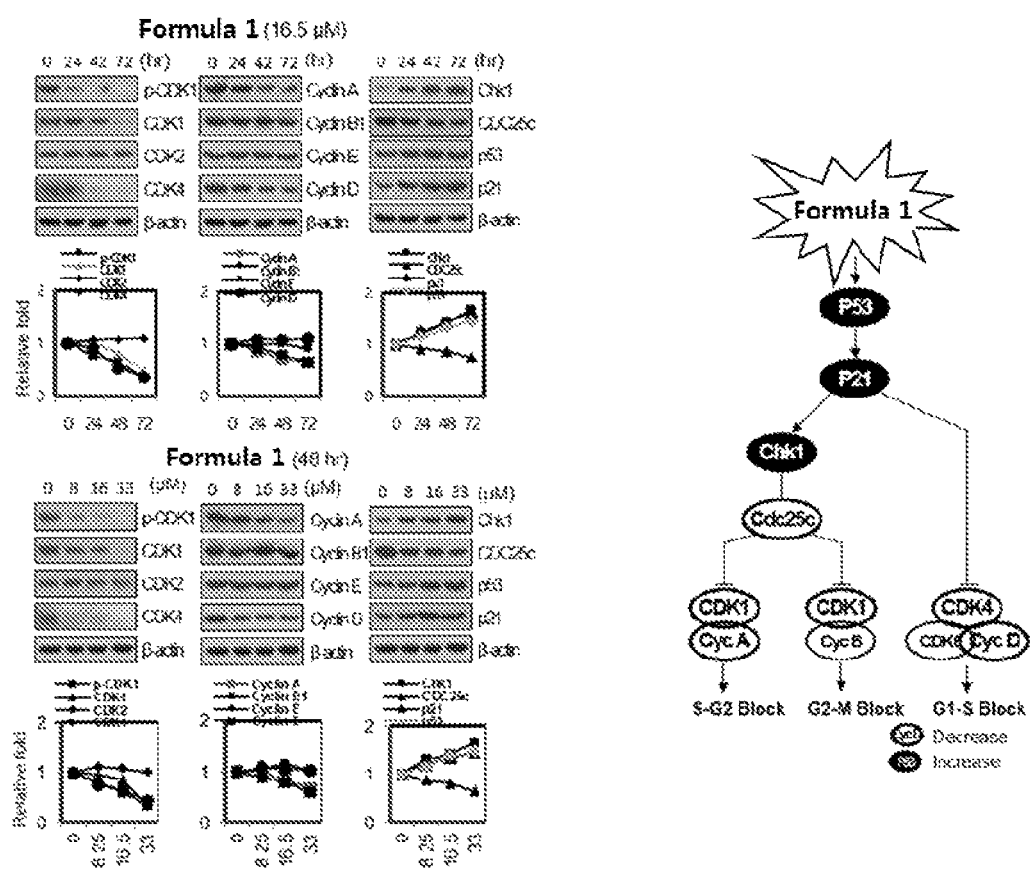

[FIG. 14]
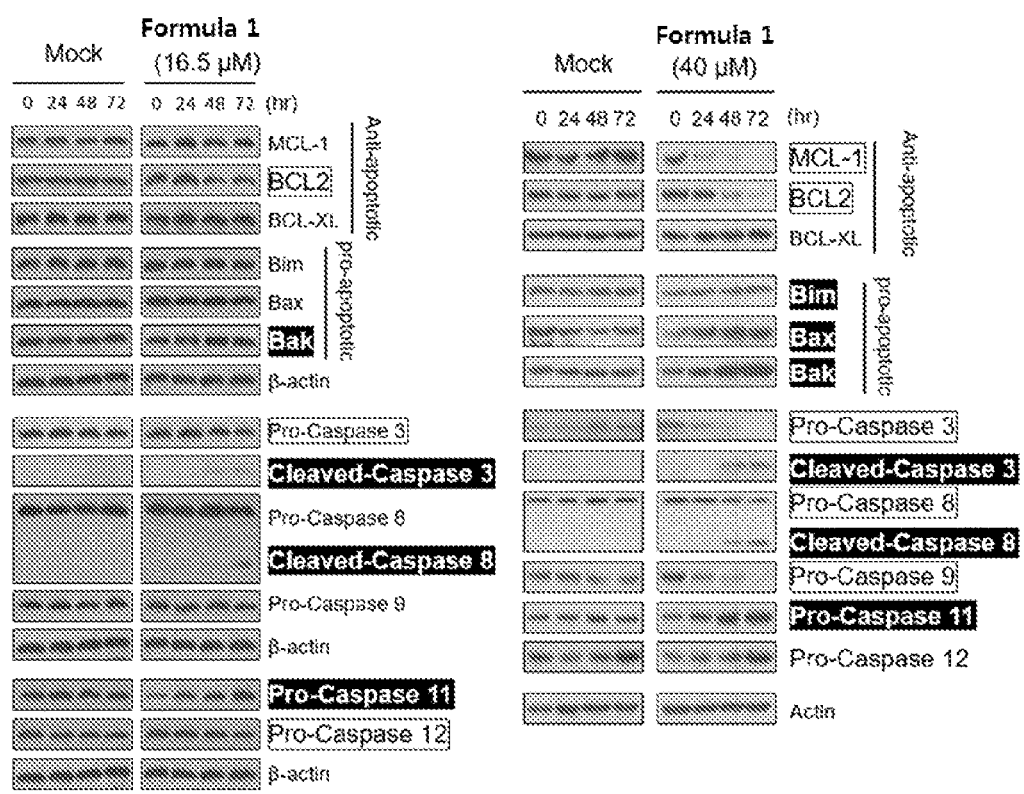

ized by a cancer cell characteristic. For example, the compound may be represented by the following Chemical Formula 1.

COMPOSITION COMPRISING COMPOUND INHIBITING INTERACTIONS OF MBD2 AND P66α FOR ANTI-METASTASIS AND PREVENTION AND TREATMENT OF CANCER DISEASE

CROSS-REFERENCE TO RELATED APPLICATION

This application claims priority to and the benefit of Korean Patent Application No. 10-2016-0157163, filed on Nov. 24, 2016 and Korean Patent Application No. 10-2016-0157164, filed Nov. 24, 2016 the disclosures of which are incorporated herein by reference in their entirety.

TECHNICAL FIELD

The present invention relates to a pharmaceutical composition including a compound inhibiting the MBD2-p66α (GATAD2A) interaction for inhibiting metastasis and preventing and treating cancer diseases.

BACKGROUND ART

Over the past several decades, numerous basic and clinical efforts to treat various diseases including cancer have been made globally, and research on signal transduction based on the action mechanisms of genes has been actively conducted to develop new therapeutic agents.

Until now, while many natural substances, protein/peptide therapeutic agents and chemically-synthetic therapeutic agents have been developed and used, in many cases, the reoccurrence of diseases even after the treatment with such therapeutic agents may occur, there may have serious side effects also on normal cells in organisms, and such therapeutic agents may not properly work depending on patients even with the same type of disease due to a variety of the causes of a disease. In addition, there is resistance to a therapeutic agent or a recurrent disease appears after the treatment with a therapeutic agent.

To date, most therapeutic agents are based on the inhibition of signaling receptors present on the surface of cancer cells and kinases/dephosphorylases important in intracellular signal transduction. However, since such receptors and enzymes are involved in the survival of normal cells, the developed anticancer agents may affect normal cells and thus have serious side effects.

Recently, the development of therapeutic agents targeting transcription factors and epigenomes, which are involved in fundamental regulation of gene expression, is also growing. However, such factors are also needed to maintain normal cells in the organisms, and therefore it is difficult to find effective targets.

An Mi-2/NuRD chromatin remodeling complex is induced by DNA methylation, thus exhibits a function of maintaining the inhibition of transcription, and includes HDAC as a component. Since the Mi-2/NuRD complex may directly bind to a DNA methylase as well as a DNA methylation site, it plays a very important role in epigenetically inhibiting gene expression, and MBD2 knock-out (MBD2 −/−) mice are known to show normal survival and proliferation and not exhibit harmful effects (Hendrich B, Guy J, Ramsahoye B, Wilson V A, Bird A, Closely related proteins MBD2 and MBD3 play distinctive but interacting roles in mouse development. Genes Dev, 2001, 15: 710), and when MBD2 expression is decreased in cancer cell line and cancer-implanted animal models, it is known to have an inhibitory effect on cancer growth (Slack A, Bovenzi V, Bigey P, Ivanov M A, Ramchandani S, Bhattacharya S, tenOever B, Lamrihi B, Scherman D, Szyf M, Antisense MBD2 gene therapy inhibits tumorigenesis. J Gene Med, 2002, 4: 381; Sansom O J, Berger J, Bishop S M, Hendrich B, Bird A, Clarke A R, Deficiency of Mbd2 suppresses intestinal tumorigenesis. Nat Genet, 2003, 34: 145; Mian O Y, Wang S Z, Zhu S Z, Gnanapragasam M N, Graham L, Bear H D, Ginder G D, Methyl-binding domain protein 2-dependent proliferation and survival of breast cancer cells. Mol Cancer Res, 2011, 9: 1152).

In previous research on a globin gene transcription regulatory mechanism by the transcription factor CP2c (also named TFCP2, LSF, LBP1, and USF) in murine erythroleukemia (MEL) cell line models, the inventors of the present invention confirmed that the attenuation of MBD2 expression is essential for normal erythrocyte differentiation. MEL cell lines are cancer cells in which differentiation is stopped in a proerythroblast stage during erythrocyte differentiation, but when the culture solution is treated with a chemical inducer such as dimethyl sulfoxide (DMSO) or hexamethylene bisacetamide (HMBA), globin gene expression occurs as well as terminal differentiation.

They also confirmed that CP2c is involved in erythrocyte-specific globin gene transcription by forming a CBP complex with CP2b and PIAS1 proteins (Kang H C, Chae J H, Lee Y H, Park M A, Shin J H, Kim S H, Ye S K, Cho Y S, Fiering S, Kim C G, Erythroid cell-specific alpha-globin gene regulation by the CP2 transcription factor family Mol Cell Biol, 2005, 25: 6005; Kang H C, Chae J H, Jeon J, Kim W, Ha D H, Shin J H, Kim C G, Kim C G, PIAS1 regulates CP2c localization and active promoter complex formation in erythroid cell-specific alpha-globin expression. Nucleic Acids Res, 2010, 38; 5456), and identified that p66α (GATAD2A), one of the components of Mi-2/NuRD CRC, directly binds to CP2c (Kang H C, Chung B M, Chae J H, Yang S I, Kim C G, Kim C G, Identification and characterization of four novel peptide motifs that recognize distinct regions of the transcription factor CP2. FEBS J, 2005, 272: 1265).

In addition, p66α inhibits the transcription activity of CBP transcription factor complexes (CP2c, CP2b and PIAS1) through binding with CP2c, and when the p66α expression-attenuated MEL cell line is intravenously injected into immunodeficient mice, tumorigenesis in the blood, spleen and liver were remarkably inhibited as well as splenomegaly shown in normal control cells. It was confirmed that the p66α expression is constantly maintained during the induction of erythrocyte differentiation in the MEL cells and erythrocyte differentiation in the bone marrow, and the expression of MBD2 as another component of Mi-2/NuRD CRC, which is known to directly bind to p66α, is rapidly reduced.

Actually, the transcription activity of the CBP complex had an inverse-correlation with MBD2 expression, and the MBD2 expression-attenuated MEL cell line showed spontaneous erythrocyte differentiation. In addition, it was confirmed that MBD2 is involved in the activity of the CBP complex by the interaction with p66α, and a new fact that Mi-2/NuRD CRC present in undifferentiated MEL cells, as typical CRC having MBD2 (restrictive Mi-2/NuRD CRC), inhibits the expression of a target gene, but permissive Mi-2/NuRD CRC that does not have MBD2 aids the transcription activity of the CBP complex while not separated from a globin gene promoter during normal erythrocyte differentiation was identified.

As such, since MBD2 does not affect the survival of normal cells, and the MBD2-p66α interaction is important for the inhibitory function of Mi-2/NuRD CRC against gene expression, it is determined that MBD2 may be an important target for the development of an anticancer agent.

DISCLOSURE

Technical Problem

Therefore, the present invention suggests a compound for suppressing or inhibiting the MBD2-p66α interaction, and is directed to providing a pharmaceutical composition including the compound for inhibiting metastasis of various types of hematological cancers and solid tumors, and preventing or treating cancer diseases.

However, technical problems to be solved in the present invention are not limited to the above-described problems, and other problems which are not described herein will be fully understood by those of ordinary skill in the art from the following description.

Technical Solution

To solve the above-mentioned object, the present invention provides a composition including an inhibitor against the function of an Mi-2/NuRD chromatin remodeling complex for inhibiting metastasis and preventing and treating cancer diseases.

The function inhibitor of the present invention may be a compound represented by Formula 1 or a pharmaceutically acceptable salt thereof.

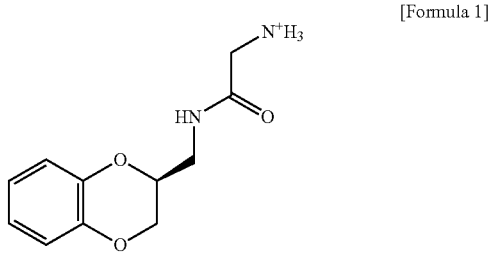

[Formula 1]

In addition, the function inhibitor of the present invention may be a compound represented by Formula 2 or a pharmaceutically acceptable salt thereof.

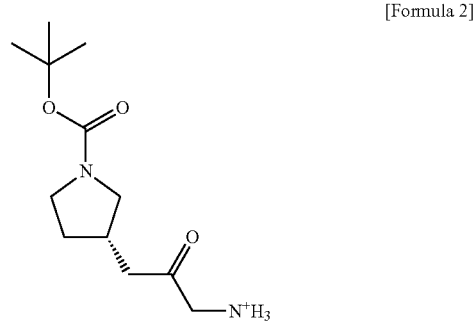

[Formula 2]

The compound represented by Formula 1 of the present invention binds to the p66α at an MBD2-p66α (GATAD2A) interaction site of the Mi-2/NuRD chromatin remodeling complex structure, thereby inhibiting the interaction with MBD2.

In addition, the compound represented by Formula 2 of the present invention binds to the MBD2 at an MBD2-p66α (GATAD2A) interaction site of the Mi-2/NuRD chromatin remodeling complex structure, thereby inhibiting the interaction with p66α.

In addition, the cancer disease may be any one selected from solid tumors of lymphoid leukemia, leukemia, colorectal cancer, lung cancer, kidney cancer, liver cancer, breast cancer and brain tumors.

In addition, the pharmaceutically acceptable salt may be one or more selected from the group consisting of hydrochloric acid, hydrobromic acid, hydroiodic acid, sulfuric acid, nitric acid, phosphoric acid, methanesulfonic acid, benzenesulfonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

Meanwhile, the term "treatment" refers to the suspension or delay of the progression of a disease when an agent is used on a subject exhibiting symptoms of a disease.

The term "pharmaceutical composition" may include a pharmaceutically acceptable carrier, diluting agent, excipient, or a combination thereof when needed as well as the compound of the present invention.

The term "pharmaceutically acceptable" refers to a property that does not damage the biological activity and property of a compound.

Unless particularly defined otherwise, other terms and abbreviations used in the specification can be interpreted as a meaning usually comprehended by those of ordinary skill in the art.

Advantageous Effects

A compound or pharmaceutically acceptable salt thereof according to the present invention can bind to p66α at an MBD2-p66α (GATAD2A) interaction site of an Mi-2/NuRD chromatin remodeling complex structure, thereby inhibiting the interaction with MBD2, or bind to MBD2, thereby inhibiting the interaction with p66α, and therefore can be effectively used as a pharmaceutical composition that can inhibit metastasis of various types of hematological cancers and solid tumors, and prevent or treat cancer diseases.

DESCRIPTION OF DRAWINGS

FIGS. 1A and 1B show data obtained by co-immunoprecipitation assay (Co-IP), indicating the ability of a compound according to the present invention to inhibit the interaction between MBD2 and p66α: FIG. 1A is the analysis result showing the ability of the compound of Formula 1 for actually inhibiting the interaction between MBD2 and p66α; and FIG. 1B is the analysis result showing the ability of a compound of Formula 2 for actually inhibiting the interaction between MBD2 and p66α.

FIGS. 2A and 2B show the data obtained by Luc reporter assay, indicating the treatment with the compounds according to the present invention induces an effect on the role of MBD2 or p66α in target gene expression of a CP2c transcription factors complex: FIG. 2A is the data obtained by the treatment with the compound of Formula 1; and FIG. 2B is the data obtained by the treatment with the compound of Formula 2.

FIGS. 3A and 3B show the data obtained by analyzing in vitro cancer cell migration and invasion abilities to confirm whether EMT and metastasis are inhibited by the treatment with the compounds according to the present invention: FIG. 3A is the data obtained by the treatment with the compound of Formula 1; and FIG. 3B is the data obtained by the treatment with the compound of Formula 2.

FIGS. 4A and 4B show the data obtained by western blotting performed 48 hours after compounds are treated to confirm whether the compounds according to the present invention affect the expression of metastasis-related marker proteins: FIG. 4A is the data obtained after an HCT116 cell line is treated with the compounds of Formula 1 and Formula 2 (086567 and 080579); and FIG. 4B is the data obtained after an MDA-MB-231 cell line is treated with the compounds of Formula 1 and Formula 2.

FIGS. 5A and 5B show the result (IC50 values) analyzed for cancer cell lines derived from various origins, indicating whether the compounds according to the present invention also affect the growth and cell death of cancer cells: FIG. 5A is the data for the compound of Formula 1 and FIG. 5B is the data for the compound of Formula 2.

FIGS. 6A and 6B show the cell viability of cell lines according to the treatment of cells lines with various types of lymphoid leukemia (Raji, Molt-4, IM-9, Jurkat, CCRF-CEM, and Daudi), curves of cell growth inhibition at 48 hours after the treatment with compounds, IC50 values and cell images: FIG. 6A is the result obtained by the treatment with the compound of Formula 1; and FIG. 6B is the result obtained by the treatment with the compound of Formula 2.

FIGS. 7A and 7B show the cell viability of cell lines according to the treatment of cells lines with 8 types of leukemia (KCL22, MEL, THP-1, HL60, HEL, U937, KG-1, and K562), curves of cell growth inhibition at 48 hours after the treatment with compounds, IC50 values and cell images: FIG. 7A is the result obtained by the treatment with the compound of Formula 1; and FIG. 7B is the result obtained by the treatment with the compound of Formula 2.

FIGS. 8A and 8B show the cell viability of cell lines according to the treatment of cells lines with 6 types of solid tumors (HCT116, Hep3B, MCF7, MDA-MB-231, MCF10A, and U373MG) and 2 types of genetically modified normal cell lines (BEAS2B, 293T), curves of cell growth inhibition at 48 hours after the treatment with compounds, IC50 values and cell images: FIG. 8A is the result obtained by the treatment with the compound of Formula 1; and FIG. 8B is the result obtained by the treatment with the compound of Formula 2.

FIGS. 9A, 9B, 9C, 9D, 9E, 9F, 9G, 9H, 9I and 9J include diagrams showing a growth inhibitory effect and a cell death inducing effect of an MEL cell line in animal models by the treatment with the compound of Formula 1 according to the present invention: FIGS. 9A, 9B, 9C, 9D and 9E include experimental data for verifying the growth inhibitory effect and cell death inducing effect of the MEL cell line by the treatment of the compound of Formula 1 at different concentrations, in which FIG. 9A shows an entire experimental design, FIG. 9B shows images of mice, spleens and livers, which are extracted therefrom, FIG. 9C shows the weights of the mice, spleens and livers, FIG. 9D shows hematological characteristics, and FIG. 9E shows the histological characteristics of major organs.

In addition, FIGS. 9F, 9G, 9H, 9I and 9J are experimental data for confirming an effect of treating a tumor in an MEL cell line according to the treatment of the compound of Formula 1 at different concentrations, wherein FIG. 9F shows an entire experimental design, FIG. 9G shows images of mice, spleens and livers, which are extracted therefrom, FIG. 9H shows the weights of the mice, spleens and livers, FIG. 9I shows hematological characteristics, and FIG. 9J shows the histological characteristics of major organs.

FIGS. 10A and 10B are a diagram showing MBD2 and p66α expression patterns in leukemia and lymphoid leukemia cell lines by the treatment with the compound of Formula 1 according to the present invention: FIG. 10A is the result confirmed from the result of western blotting, and FIG. 10B shows relative folds.

FIG. 11 is a diagram showing the result of analyzing the cell cycle of MEL cells by the treatment with the compound of Formula 1 according to the present invention.

FIG. 12 is a diagram showing the result of analyzing an effect of inducing aneuploidy of MEL cells by the treatment with the compound of Formula 1 according to the present invention.

FIG. 13 is a diagram showing the result of analyzing cell cycle-related marker protein expression in MEL cells by the treatment with the compound of Formula 1 according to the present invention.

FIG. 14 is a diagram showing the result of analyzing cell death-related labeling gene expression in MEL cells by the treatment with the compound of Formula 1 according to the present invention.

MODES OF THE INVENTION

Hereinafter, the present invention will be described in further detail.

The present invention relates to a composition including an inhibitor against the function of an Mi-2/NuRD chromatin remodeling complex as an active ingredient for inhibiting metastasis and preventing and treating cancer diseases.

In the present invention, the function inhibitor may be a compound represented by Formula 1 or Formula 2, or a pharmaceutically acceptable salt thereof.

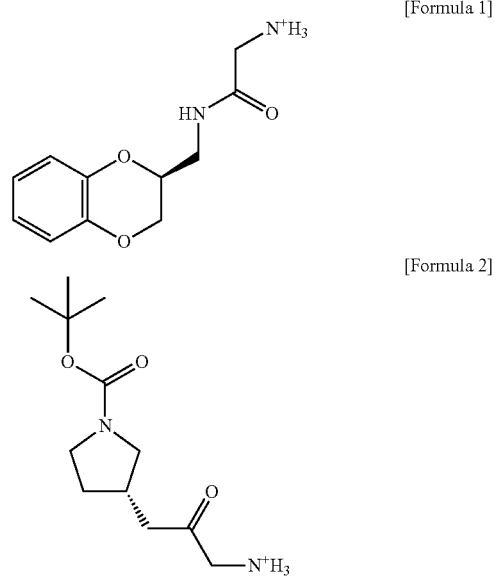

[Formula 1]

[Formula 2]

The compound represented by Formula 1 according to the present invention, as can be confirmed in an example that will be described below, binds to p66α at an MBD2-p66α

(GATAD2A) interaction site of an Mi-2/NuRD chromatin remodeling complex structure, thereby inhibiting the interaction with MBD2.

In addition, the compound represented by Formula 2 according to the present invention, as can be confirmed in an example that will be described below, binds to MBD2 at an MBD2-p66α (GATAD2A) interaction site of an Mi-2/NuRD chromatin remodeling complex structure, thereby inhibiting the interaction with p66α.

In addition, the cancer disease may be any one selected from solid tumors of lymphoid leukemia, leukemia, colorectal cancer, lung cancer, kidney cancer, liver cancer, breast cancer and brain tumors, and preferably leukemia.

Meanwhile, in the present invention, pharmaceutically acceptable salts may be acid addition salts formed of acids forming a pharmaceutically acceptable nontoxic acid addition salt containing an anion, for example, inorganic acids such as sulfuric acid, hydrochloric acid, nitric acid, phosphoric acid, hydrobromic acid, and hydriodic acid, organic acids such as tartaric acid, formic acid, citric acid, acetic acid, trifluoroacetic acid, gluconic acid, benzoic acid, lactic acid, fumaric acid, lactic acid, malonic acid, malic acid, salicylic acid, succinic acid, oxalic acid, propionic acid, aspartic acid, glutamic acid, and citric acid, and sulfonic acids such as methanesulfonic acid, ethanesulfonic acid, benzenesulfonic acid, p-toluenesulfonic acid, and naphthalenesulfonic acid, and also sodium, calcium and ammonium salts as well as the acid addition salts; and pharmaceutically acceptable base addition salts, for example, alkali metal or alkaline earth metal salts formed of lithium, sodium, potassium calcium and magnesium, amino acid salts such as lysine, arginine, and guanine, and organic salts such as dicyclohexylamine, N-methyl-D-glucamine, tris(hydroxymethyl)methylamine, diethanolamine, choline, and triethyl amine.

In addition, according to various exemplary embodiments of the present invention, a salt dissolved in a buffer solution is used as a diluting agent, and a conventionally used buffer solution may be phosphate buffered saline imitating a salt form of a human solution. Since a buffer salt may control the pH of a solution at a low concentration, a buffer diluting agent does not change the biological activity of a compound.

The compound according to the present invention may be formulated in various forms to be used as a pharmaceutical or veterinary composition containing a pharmaceutically or veterinarily acceptable carriers or diluting agents. The composition according to the present invention may be prepared according to a conventional method, and administered in a pharmaceutically or veterinarily suitable form.

According to an exemplary embodiment of the present invention, the composition may be administered in the form of a tablet, capsule, sugar-coated tablet, film-coated tablet, a liquid solution or a suspension, or administered parenterally, for example, by subcutaneous, intramuscular or intravenous injection.

A dosage may be determined according to various factors including a patient's age, body weight and condition, and an administration route. A daily dose may be changed within a wide range of threshold values, and may be adjusted for individual conditions. However, generally, when the compound of the present invention is administered alone to an adult, a dose selected depending on a route may be 0.0001 to 50 mg/kg of body weight, for example, 0.01 to 1 mg/kg of body weight in the range of 0.001 to 10 mg/kg of body weight.

Such a dose may be provided, for example, 1 to 5 times a day. In the case of intravenous injection, a suitable daily dose may be 0.0001 to 1 mg/kg of body weight, and preferably 0.0001 to 0.1 mg/kg of body weight. The daily dose may be administered as a single dose, or according to a fractionated dose schedule.

Hereinafter, the present invention will be described in further detail based on the action mechanisms and effects of the compounds of Formulas 1 and 2 according to the present invention.

EXAMPLES

1. Confirmation of Inhibition of MBD2-p66α Interaction of Compound According to the Present Invention Co-immunoprecipitation assay (Co-IP) was carried out on compounds of Formulas 1 and 2 according to the present invention to confirm whether the interaction between MBD2 and p66α may be actually inhibited, and the results are shown in FIGS. 1A and 1B.

As a result of Co-IP performed after a cell extract obtained by transducing a 293T cell line with vectors for overexpressing MBD2 and p66α proteins labeled with 3XFB and Myc, respectively, was treated with a compound, it can be confirmed that the compound according to the present invention concentration-dependently inhibits the binding between MBD2 and p66α.

The inventors of the present invention have confirmed in previous research that the expression of a target gene via a CP2c transcription factor complex may be inhibited by MBD2 or p66α overexpression as well as intact Mi-2/NuRD CRC, and the expression of a target gene, however, is restored by inhibiting the interaction between MBD2 and p66α as well as by the attenuation of MBD2 or p66α expression.

Therefore, Luc reporter assay was carried out to analyze whether a decrease in the target gene expression of the CP2c transcription factor complex due to MBD2 or p66α overexpression is restored by the treatment with a compound for inhibiting the interaction between the MBD2 and p66α selected in the previous step (FIGS. 2A and 2B). Here, as a CP2c transcription factor target sequence that controls Luc reporter gene expression, a GATA1 enhancer was used, and 293T cells were transduced with various combinations of CBP complex protein overexpression vectors and then used for analysis.

As a result, as shown in FIG. 2A, the compound of Formula 1 restored the inhibition of target gene expression by p66α overexpression, but did not restore the inhibition of target gene expression by MBD2 overexpression.

In addition, as shown in FIG. 2B, the compound of Formula 2 restored the inhibition of target gene expression by MBD2 overexpression, but did not restore the inhibition of target gene expression by p66α overexpression.

Therefore, it was confirmed that the compound of Formula 1 binds to p66α and thus inhibits the interaction with MBD2, and the compound of Formula 2 binds to MBD2 and thus inhibits the interaction with p66α.

2. Analysis of Metastasis Inhibitory Ability of Compound According to the Present Invention A phenomenon in which epithelial cells are converted into mesenchymal cells is called the epithelial to mesenchymal transition (EMT), and EMT-occurring cells enter blood vessels and lymph nodes due to losing an adhesive ability between cells and acquiring a migration ability, thereby forming metastatic cancer.

As major transcription factors involved in EMT induction, Twist, Snail, Slug, and Zeb1/2 have been known, and particularly, it has been reported that Twist, recently known as a major regulator for EMT and metastasis, interacts with Mi-2/NuRD CRC, and because of attenuated expression of an Mi-2/NuRD CRC constitutive protein, inhibition of the expression of the E-cadherin gene, which is one of the target genes of Twist, is restored, and EMT is inhibited (Fu J, Qin L, He T et al., The TWIST/Mi-2/NuRD protein complex and its essential role in metastasis. Cell Res, 2011, 21: 275).

Accordingly, to confirm whether EMT and metastasis are inhibited by the treatment with the compounds of Formulas 1 and 2, in vitro cancer cell migration and invasion abilities were analyzed, and the result is shown in FIGS. 3A and 3B below.

After two types of solid tumor cell lines (MDA-MB-231 breast cancer cell line and HCT116 colorectal cancer cell line) and two types of blood cell cancers (MEL murine erythroleukemia cell line and HL60 human promyelocytic leukemia cell line) were treated with 10 μM of a compound using a Trans-well insert, as a result of analyses of migration and invasion abilities, as shown in FIGS. 3A and 3B, it can be confirmed that the compounds of Formulas 1 and 2 showed a significant inhibitory effect on migration and invasion abilities in comparison with controls in all cell lines, and showed very excellent migration and invasion inhibitory effects.

In addition, as a result of confirming the expression of EMT-associated marker proteins by western blotting, after the colorectal cancer cell line HCT116 and breast cancer cell line MDA-MB-231 cell line was treated with 10 μM of each compound, according to another experiment, to see whether EMT and metastasis are inhibited by the compounds of Formulas 1 and 2 according to the present invention, as shown in FIGS. 4A and 4B, the expression of epithelial cell marker proteins (β-catenin, E-cadherin) was decreased, but the expression of mesenchymal cell marker proteins (Snail, slug, N-cadherin) was significantly decreased (FIGS. 4A and 4B). Therefore, the compounds of Formulas 1 and 2 according to the present invention may be excellent leading materials in the development of therapeutic agents for metastasis.

3. Analysis of Anticancer Efficiency of Compound According to the Present Invention Analyses were carried out for cancer cell lines derived from various origins to see whether the compounds of Formulas 1 and 2 according to the present invention affect the growth and cell death of cancer cells, and the results were summarized and are shown in FIGS. 5A and 5B below.

Lymphoid leukemia cell lines (Raji, Molt4, IM9, Jurkat, CCRF-CEM, and Daudi), leukemia cell lines (KCL22, MEL, THP-1, HL60, HEL, U937, KG-1, and K562), and solid tumor cell lines (HCT116 colorectal cancer cell line, BEAS2B lung epithelial cell line, 293T fetus kidney epithelial cell line, Hep3B liver cancer cell line, MCF7 and MDA-MB-231 breast cancer cell lines, MCF10A breast epithelial cell line, and U373MG brain tumor cell line) were treated with a compound at different concentrations (0, 1, 10, 100, 1,000, and 10,000 μM), cultured for 4 days, and subjected to MTT assay every 24 hours to measure cell viability. 48 hours after the treatment with the compound, a morphological change of the cells was observed, and cell images were taken. IC50 values caused by the treatment with each compound were calculated using the Graph Prism Pad 6 program.

In addition, the cell viabilities of 6 types of lymphoid leukemia (Raji, Molt-4, IM-9, Jurkat, CCRF-CEM, Daudi), 8 types of leukemia (KCL22, MEL, THP-1, HL60, HEL, U937, KG-1, K562) and 6 types of solid tumors (HCT116, Hep3B, MCF7, MDA-MB-231, MCF10A, U373MG) and 2 types of genetically modified normal (BEAS2B, 293T) cell lines, cell growth inhibition curves plotted at 48 hours after the treatment with the compound, IC50 values, and cell images are shown in FIGS. 6A, 6B, 7A, 7B, 8A and 8B below.

Taken together, as shown in FIGS. 6A, 7A and 8A, although there were great differences depending on cancer cell lines, overall, the lowest IC50 values (6 to 218 μM, average 50 μM) of the compound of Formula 1 were shown in the leukemia cell line, slightly higher IC50 values such as 213 μM and 1776 μM (average) were shown in lymphoid leukemia and solid tumor cell lines, respectively.

Therefore, it can be noted that the compound of Formula 1 according to the present invention can be used as a composition for treating, for example, leukemia.

In addition, as shown in FIGS. 6B, 7B and 8B, taken together, it can be noted that the compound of Formula 2 shows slightly higher IC50 values, which were uniform results in all cancer cell lines, but has effects of inhibiting the growth and inducing cell death of cell lines in various cancer cell lines.

Therefore, it can be noted that the compound of Formula 2 according to the present invention binds to MBD2 in the leukemia cell line expressing p66α at a low concentration and thereby effectively inhibits the function of permissive Mi-2/NuRD CRC which promotes target gene expression, resulting in an anticancer effect.

4. Analysis of Anticancer Effect in Leukemia Cell Line-Implanted Animal Models

Whether a leukemia cell line-specific cell death inducing phenomenon caused by the compound of Formula 1 of the present invention occurs even in the leukemia cell line-implanted animal models was analyzed.

The inventors of the present invention had identified in previous research that tumorigenesis in the blood, spleen and liver occurs as well as splenomegaly due to the intravenous injection with the MEL cell line in immunodeficient mice, and verified the effects of inhibiting the growth and inducing cell death of the MEL cell line according to the treatment with the compound of Formula 1 in animal models according to the present invention. The result is shown in FIGS. 9A, 9B, 9C, 9D, 9E, 9F, 9G, 9H, 9I and 9J below.

After the MEL cell line was intravenously injected into the immunodeficient mice, and the compound of Formula 1 was also intravenously injected at three different concentrations (12.2, 24.4, and 48.8 μg/Kg) five times at intervals of three days, on the 16$^{th}$ day, the mice were sacrificed to measure weights of the spleen and the liver and perform comparative analyses of histological/hematological characteristics of the major organs and blood, as a result, it was confirmed that splenomegaly caused by the MEL cells disappeared due to the concentration-dependent administration of the compound, and there were no tumor cells in the blood, spleen and liver (FIGS. 9A, 9B, 9C, 9D and 9E). However, a white blood cell level was reduced due to the treatment with the compound at a slightly higher concentration, but the histological characteristics of the major organs as well as the overall hematological characteristics were normal (FIGS. 9D and 9E).

Meanwhile, to confirm whether the compound of Formula 1 can treat tumors generated in the animal models, the MEL cell line was intravenously injected, after 7 days, the compound of Formula 1 was intravenously injected five times at intervals of three days, and then, on the 21$^{th}$ day, the mice were sacrificed to be subjected to analysis by the above-described method (FIG. 9F).

It was confirmed that splenomegaly caused by the MEL cells disappeared due to the concentration-dependent administration of the compound of Formula 1, there were no tumor cells in the blood, spleen and liver, and the histological characteristics of the major organs as well as the overall hematological characteristics were normal (FIGS. 9G, 9H, 9I and 9J).

Therefore, it can be noted that the compound of Formula 1 according to the present invention effectively inhibits the growth of the implanted MEL cell line and effectively controls cells of the formed tumor, but there were no side effects in normal tissue/blood.

5. Analysis of Action Mechanism of Leukemia-Specific Anticancer Effect

To analyze why the compound of Formula 1 according to the present invention has a specifically lower IC50 value in the leukemia cell line, intracellular MBD2 and p66α protein expression levels in the lymphoid leukemia cell line and the leukemia cell line were quantitatively analyzed by performing western blotting.

As a result, referring to FIGS. 10A and 10B below, it can be confirmed that the relative expression of MBD2 is lower than p66α in the leukemia cell line, unlike the lymphoid leukemia cell line.

The inventors of the present invention have confirmed in the previous research that MBD2-containing Mi-2/NuRD CRC inhibits target gene expression in an undifferentiated erythroleukemia cell line (proerythroid stage), and MBD2 expression is remarkably reduced by inducing terminal differentiation of erythrocytes, and thus MBD2-free Mi-2/NuRD CRC promotes target gene expression.

Accordingly, in the leukemia cell line, due to low MBD2 expression, MBD2-deficient Mi-2/NuRD CRC is expected to promote target gene expression, and it can be inferred and confirmed that the activity of target gene expression of Mi-2/NuRD CRC is inhibited by binding the compound of Formula 1 of the present invention to p66α, and thus an anticancer effect is exhibited at the low IC50 value specific to the leukemia cell line.

Meanwhile, to analyze the cause of the inhibition of cell growth and tumorigenesis abilities in the leukemia cell line by the compound of Formula 1, the change in cell cycle according to the treatment of the MEL cell line with a compound was analyzed by FACS, as a result, significant increases in subG1 (cell group dying by apoptosis) and aneuploidy (aneuploidy cell group; cells having high intracellular DNA levels by inhibiting cell division) as well as a reduction in a G0/G1 group and an increase in a G2/M group were shown as in FIG. 11 below.

As a result of the change in cell cycle measured by FACS after the cell cycle was synchronized with G1/S phases by a thymidine double block method and treating cells with the compound, it was reconfirmed that aneuploidy was remarkably induced, and according to karyotype analysis to see whether the compound actually induces the aneuploidy of the MEL cells, it was confirmed with reference to FIG. 12 that chromosomes were abnormally increased.

In addition, as a western blotting result to show the change in the expression of cell cycle-associated marker proteins according to the concentration and time of the treated compound of Formula 1, it was confirmed that all activities of cyclin/CDK controlling the checkpoints of the cell cycle were decreased. Therefore, referring to FIG. 13, it was seen that overall progression of the cell cycle was inhibited by the treatment with the compound of Formula 1, and aneuploidy and cell death were induced.

To confirm that cell death caused by the treatment with the compound of Formula 1 is induced by apoptosis, changes in the expression of apoptosis promotion and inhibition-associated marker proteins according to time after the compound was treated under the condition of two different concentrations (16.5 μM and 40 μM) was analyzed by western blotting, and thereby, as shown in FIG. 14, it was identified that the expression of the apoptosis inhibition marker was decreased, the expression of the apoptosis promotion marker was increased, and apoptosis-associated caspases were activated.

Consequently, it can be noted that the compound of Formula 1 according to the present invention binds to p66α in a leukemia cell line expressing MBD2 at a low concentration and thus effectively inhibits the function of the permissive Mi-2/NuRD CRC promoting target gene expression, and the compound of Formula 2 binds to MBD2 in a leukemia cell line expressing p66α at a low concentration and thus effectively inhibits the function of permissive Mi-2/NuRD CRC promoting target gene expression, resulting in an anticancer effect.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method for treating cancer disease or cancer metastasis comprising administering the compound represented by Formula 1 below or a pharmaceutically acceptable salt thereof:

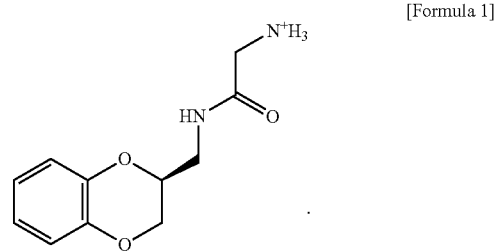

[Formula 1]

2. A method for treating cancer disease or cancer metastasis comprising administering the compound represented by Formula 2 below or a pharmaceutically acceptable salt thereof:

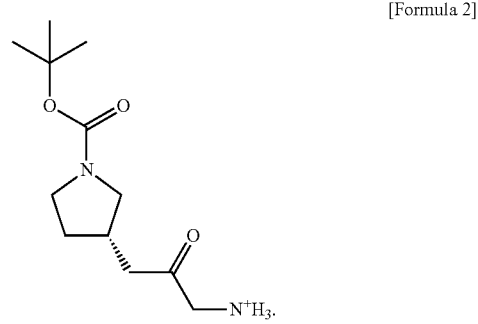

[Formula 2]

3. The method of claim 1, wherein the compound represented by Formula 1 binds to p66α at an MBD2-p66α

(GATAD2A) interaction site of an Mi-2/NuRD chromatin remodeling complex structure, and thus inhibits the interaction with MBD2.

4. The method of claim 2, wherein the compound represented by Formula 2 binds to MBD2 at an MBD2-p66α (GATAD2A) interaction site of an Mi-2/NuRD chromatin remodeling complex structure, and thus inhibits the interaction with p66α.

5. The method of claim 1, wherein the cancer disease is any one selected from tumors of lymphoid leukemia, leukemia, colorectal cancer, lung cancer, kidney cancer, liver cancer, breast cancer and brain tumors.

6. The method of claim 2, wherein the cancer disease is any one selected from tumors of lymphoid leukemia, leukemia, colorectal cancer, lung cancer, kidney cancer, liver cancer, breast cancer and brain tumors.

* * * * *